United States Patent [19]

Termanini

[11] 4,204,528
[45] May 27, 1980

[54] METHOD AND APPARATUS FOR FIBER-OPTIC INTRAVASCULAR ENDOSCOPY

[75] Inventor: Zafer A. Termanini, Brooklyn, N.Y.

[73] Assignee: Zafmedico Corp., Brooklyn, N.Y.

[21] Appl. No.: 776,302

[22] Filed: Mar. 10, 1977

[51] Int. Cl.$^2$ .............................................. A61B 1/06
[52] U.S. Cl. ........................................ 128/6; 354/62
[58] Field of Search ................ 128/6, 7, 8, 2 R, 2 S, 128/2.05 R, 303.1, 303.11, 348, 4, 5, 666, 668, 708, 737, 772; 354/62, 63, 75, 76; 350/96.26

[56] References Cited

U.S. PATENT DOCUMENTS

| 2,940,370 | 6/1960 | Yandell | 354/63 |
|---|---|---|---|
| 3,162,190 | 12/1964 | Del Gizzo | 128/6 |
| 3,583,393 | 6/1971 | Takahashi | 128/4 |
| 3,643,653 | 2/1972 | Takahashi et al. | 128/6 |
| 3,814,081 | 6/1974 | Mori | 128/2 L |
| 3,888,237 | 6/1975 | Mori | 128/6 |
| 3,903,877 | 9/1975 | Terada | 128/6 |
| 3,924,608 | 12/1975 | Mitsui | 128/6 |

FOREIGN PATENT DOCUMENTS 1058694  6/1959  Fed. Rep. of Germany .............. 128/4

OTHER PUBLICATIONS

Olympus "EF" Esophago Fiber Scope; Ad. in Medical—Surgical Review, 1st Quarter 1969.

Primary Examiner—Robert W. Michell
Assistant Examiner—Arthur S. Rose
Attorney, Agent, or Firm—Hubbell, Cohen, Stiefel & Gross

[57] ABSTRACT

Improved method for in situ visual examination of cardiovascular system comprises feeding a catheter having at least one afferent fiber-optic bundle for transmitting light from the proximal end of the catheter to the distal end thereof and at least one efferent fiber-optic bundle for returning light from the distal end to the proximal end, into the cardiovascular system until the distal end is in the vicinity of the region of cardiovascular system to be examined; illuminating the region by illuminating the proximal end of the catheter; injecting a clear physiologically innocuous fluid in front of the distal end of the catheter to increase clarity of blood in the region being examined; and observing the image returned to the proximal end of the efferent fiber-optic bundle. Fiber-optic catheter system and improved catheter for carrying out method are also disclosed.

22 Claims, 7 Drawing Figures

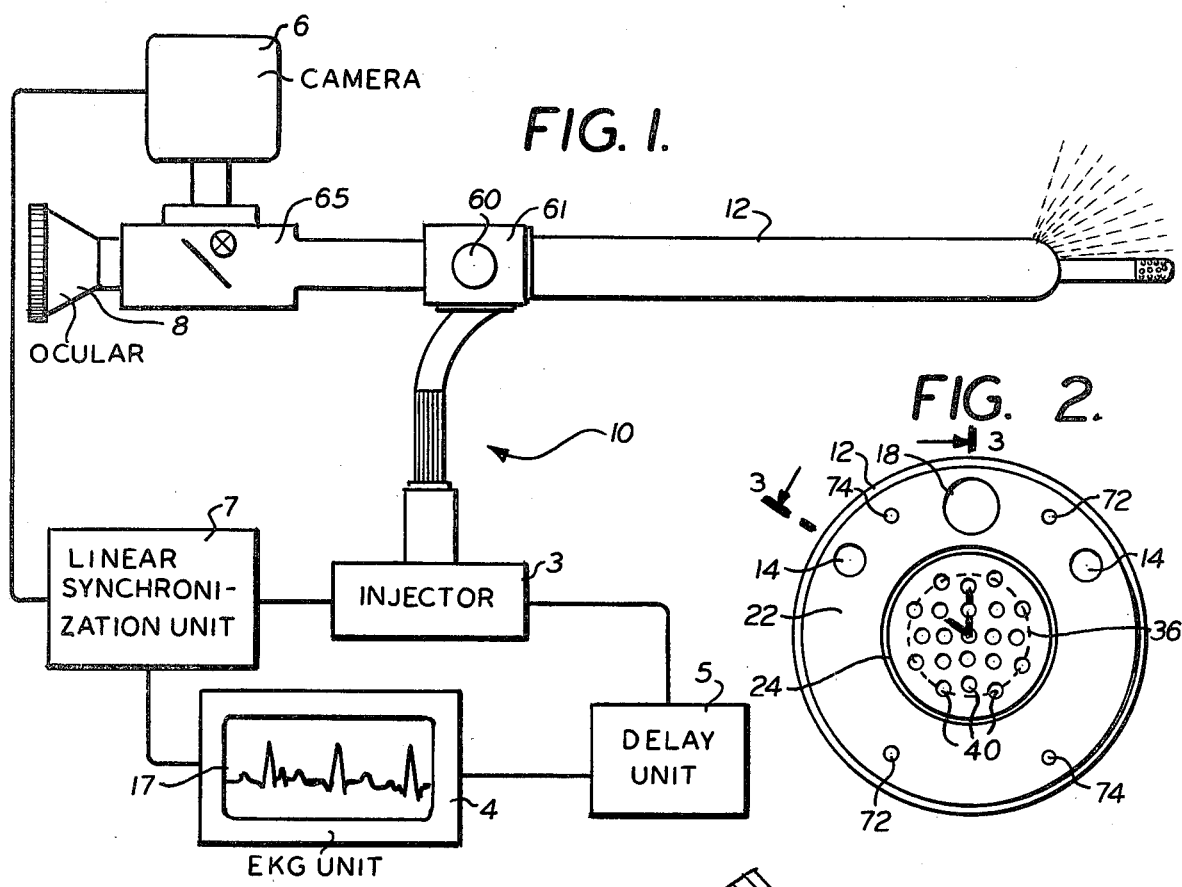
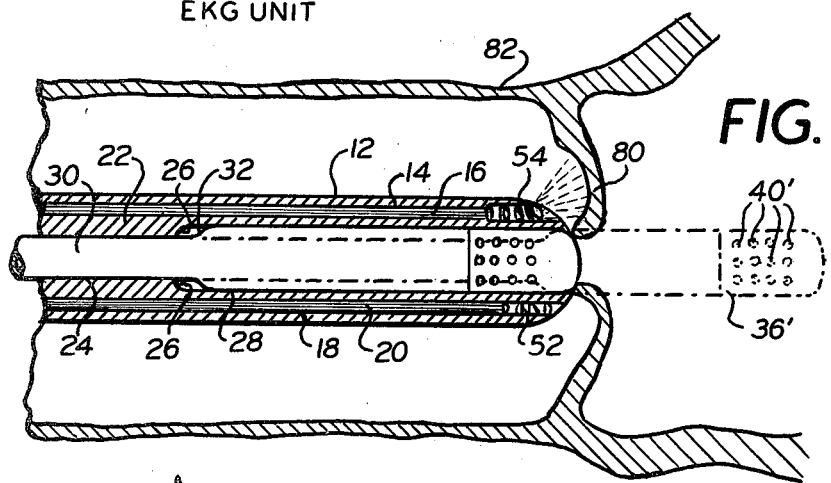
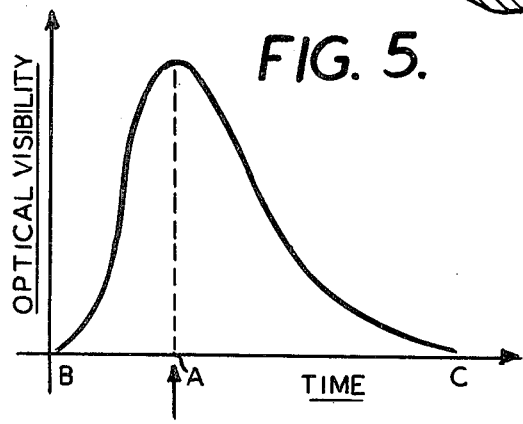
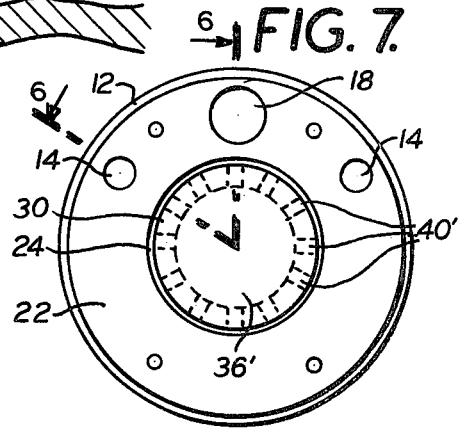

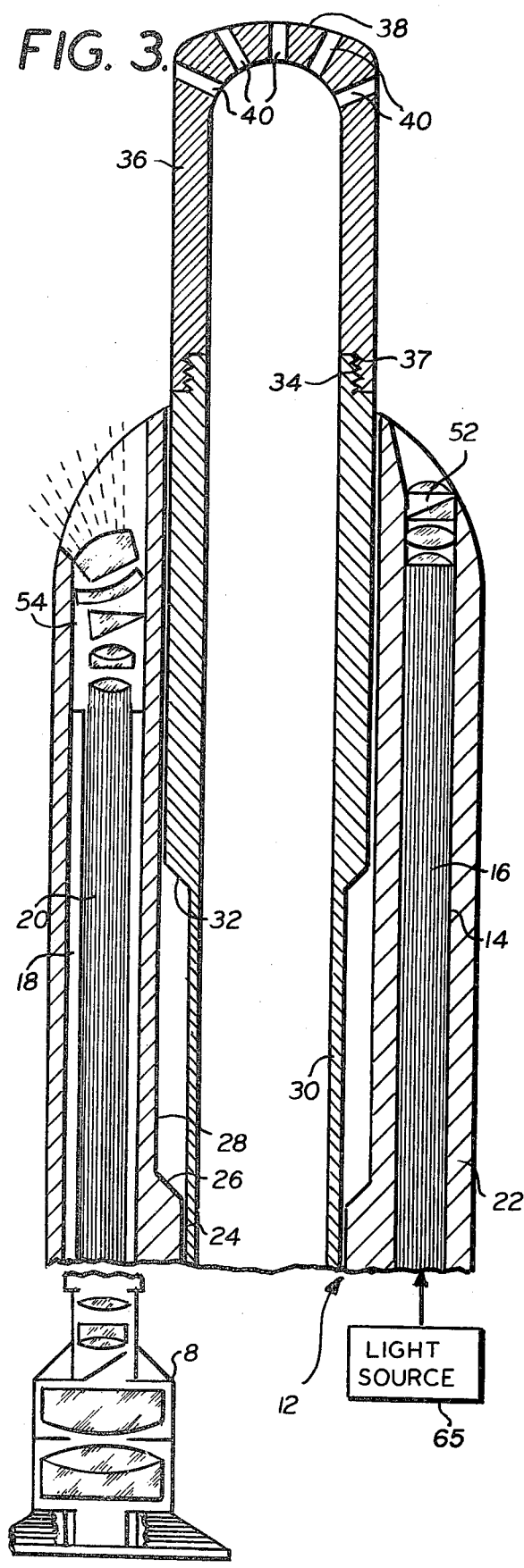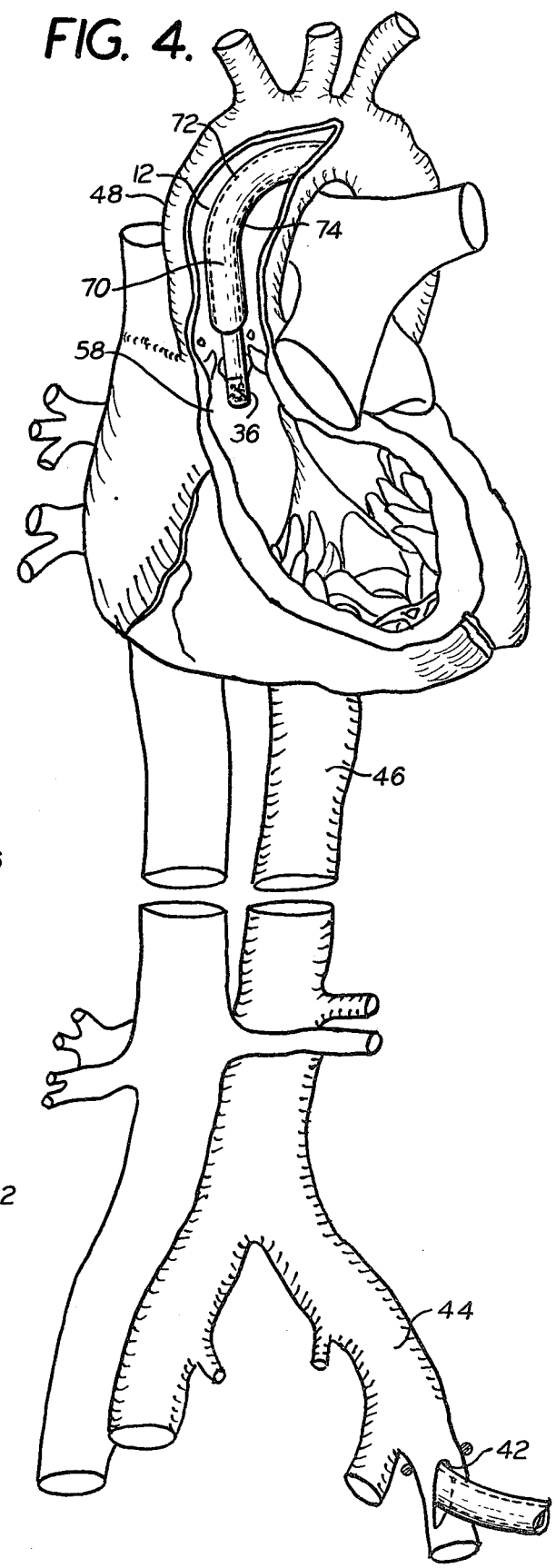

METHOD AND APPARATUS FOR FIBER-OPTIC INTRAVASCULAR ENDOSCOPY

BACKGROUND OF THE INVENTION

1. Field of the Invention

This invention pertains to cardiovascular fiber-optic endoscopy systems and methods, and to fiber-optic catheters employed therewith.

2. Prior Art

Fiber-optic catheters are well known and have been employed for a variety of purposes. Among such purposes are the monitoring of blood oxygen saturation and the measurement of intra-cardiac or intra-vascular pressure. Catheters suitable for such use are disclosed in U.S. Pat. Nos. 3,123,006, 3,822,695 and 3,814,081. It is also known to include a longitudinally extending lumen in a catheter which may be used for monitoring blood pressure, withdrawing samples of blood, or introducing medication. Such catheters are disclosed in U.S. Pat. Nos. 3,498,286, 3,807,390 and German Patent Publication No. 2,023,318.

Heretofore, the use of fiber-optic catheters for visual inspection of the cardiovascular system, as opposed to their use as tools for permitting intra-cardiovascular measurement of certain blood characteristics, has been severely restricted by the opaque quality of blood. None of the prior art known to applicant discloses a fiber-optic endoscopic catheter system which has overcome this problem. Such optical inspection is extremely useful as it would permit a search for constrictions, blockages, etc. without the necessity of complicated and hazardous surgical procedures.

SUMMARY OF THE INVENTION

According to the present invention, I have developed a fiber-optic catheter system and method of employing same particularly adapted for visual inspection of the intra-cardiovascular system. One of the principal components of the system is an improved fiber-optic catheter which includes the usual afferent and efferent light conducting fiber-optic bundles. A preferably centrally located lumen extends the length of the catheter from the distal to the proximal end thereof. A flexible tube having a preferably removable rigid head is slidably received in the lumen, the tube being movable between an extended position in which the head protrudes beyond the distal end of the catheter and a retracted position in which the head is substantially flush with the distal end of the lumen. The head is apertured to permit injection of a clear solution, such as, for example, a saline solution through the tube and into the blood whereby to reduce the opacity of the blood to permit visual or photographic inspection of a part of the cardiovascular system.

In preferred use, fluid injection into the blood is controlled by an injector which is synchronized with the patient's heartbeat whereby injection occurs a brief interval after the R-wave portion of the patient's EKG. Thus, as the clear saline solution enters the blood, it is immediately carried back toward the distal end of the catheter thereby momentarily creating a clear pocket between the optics located at the distal face of the catheter and the region of the cardiovascular system to be explored. This permits viewing through a clear medium (saline solution) as opposed to an opaque medium (blood) thus greatly enhancing the quality of visualization that is obtainable.

Preferably, a camera, synchronized with the injection apparatus, photographs the image conveyed from the distal end of the catheter upon each injection of the saline solution. In the preferred embodiment, angulation cords extending from the proximal to the distal end of the catheter are employed whereby the cords may be tensioned at the proximal end to avoid jerking of the head and possible damage to the patient during the injection procedure.

Further features and advantages of the system and method in accordance with the present invention will become more fully apparent from the following detailed description and the annexed drawings which disclose certain non-limiting examples of embodiments preferred at present.

BRIEF DESCRIPTION OF THE DRAWINGS

FIG. 1 is a diagrammatic representation of a fiber-optic catheter system in accordance with the present invention;

FIG. 2 is a view in front elevation of the preferred catheter of the present invention;

FIG. 3 is a fragmentary sectional view taken along the lines 3—3 of FIG. 2 showing the spray head in the extended position and also showing the viewing apparatus;

FIG. 4 is a perspective view showing the preferred catheter of the present invention inserted into the left ventricle;

FIG. 5 is a graph qualitatively illustrating the improved visibility which may be obtained by employing cardiovascular endoscopic techniques in accordance with the present invention;

FIG. 6 is a fragmentary sectional view similar to FIG. 3 in which the catheter is being employed to observe a valve, and also showing an alternative catheter spray head; and FIG. 7 is a view in front elevation of the catheter illustrated in FIG. 6.

DETAILED DESCRIPTION OF THE PREFERRED EMBODIMENTS

Referring now to the drawings in detail and particularly to FIG. 1 thereof, the preferred synchronized fiber-optic endoscope system 10 in accordance with the present invention is shown.

As illustrated, the system includes a fiber-optic catheter 12, a fluid injecting apparatus 3, an EKG unit 4, a delay unit 5, a camera 6, a synchronization unit 7 and ocular 8.

Referring now to FIGS. 2 and 3, fiber-optic catheter 12 comprises a length of standard cardiac catheter tubing having preferably two bundles 14 of afferent light-conducting fibers 16 and preferably one bundle 18 of efferent light-conducting fibers 20. As shown, bundles 14, 18 are enclosed within a flexible sheath 22, which has a preferably centrally located lumen 24 extending longitudinally therethrough. The construction of a suitable flexible catheter sheath 22 is well known in the art. By way of example, sheath 22 may be comprised of rubber, a synthetic plastic or, preferably, a silicone rubber laminate.

Preferably, the cross section of lumen 24 is circular and is stepped outwardly near the distal end of the catheter 12 to define a shoulder 26 and a widened lumen portion 28. In the preferred embodiment, the outside diameter of the catheter 12 is approximately 8 mm., while the diameter of the lumen 24 is approximately 4 mm. Preferably, the distance from shoulder 26 to the distal end of catheter 12 is about 2 cm.

As shown, a length of flexible tubing 30 is disposed for sliding movement within the lumen 24. As will be more fully described hereinafter, tubing 30 serves to carry a liquid solution from the proximal end of the catheter 12 to the distal end thereof. Tubing 30 is preferably stepped outward at the distal end to define a shoulder 32 that is complementary to catheter shoulder 26. As will become more fully apparent hereinafter, as tubing 30 is retracted toward the proximal end of the catheter 12, shoulder 32 engages shoulder 26 and thereby defines the fully retracted position of the tubing 30. Preferably, the widened portion of tubing 30 past shoulder 32 is externally threaded at 34 whereby spray head 36, having an internally threaded narrow base portion 37, may be removably secured to the distal end of the tubing 30.

Tubing 30, like sheath 22, must be flexible to permit bending as the catheter 12 is fed through the blood vessels. Thus, tubing 30 is also preferably constructed of a silicone rubber laminate and is desirably reinforced with wire mesh. Unlike sheath 22 and tubing 30, however, head 36 is preferably rigid, although not necessarily, and comprised of plastic, stainless steel, or other non-reactive material such as, for example, nickel or chromium or nickel-chromium steels. As shown, the outside diameter of the head 36 is substantially equal to the diameter of the widened portion 28 of lumen 24 while the distance from the free end of head 36 to shoulder 32 is approximately equal to the distance from shoulder 26 to the distal end of catheter 12. In addition, and is best as shown in FIG. 6, the curvature of terminus 38 of head 36 is such that when the tubing 30 is in the fully retracted position the terminus of the head and the distal end of the sheath 22 together define a smooth rounded surface which permits the catheter to be fed into the cardiovascular system without damaging the interior walls thereof. As illustrated, terminus 38 of head 36 is provided with a plurality of apertures 40 for reasons that will be more fully explained hereinafter, although one aperture may be employed.

Referring now to FIGS. 1 through 4 in detail, the use of system 10 in conjunction with intra-cardiac endoscopy will now be described. Catheter 12 is first inserted into the heart 48 by making, for example, a left femoral cut down 42 and then feeding catheter 12 through the left femoral artery 44, the aorta 46 and then into the heart 48.

During the insertion procedure, head 36, which, being constructed of a rigid material capable of causing damage to the interior side walls of the patient's cariovascular system, is held in the retracted position in which shoulder 32 engages shoulder 26. Light from a suitable light source 65 is introduced into the optical fibers 16 which comprise the bundles 14 for conductance through the catheter 12 and emission at the distal end thereof into the blood stream. Preferably, the distal ends of the bundles 14 confront suitable wide angle lens arrays 52 which provide wide angle dispersion of the emitted light. Since such lenses 52 are well known in the art and capable of ready construction by the skilled art worker, further description thereof is deemed unnecessary. Light from source 65, upon entering the blood, becomes diffusely reflected back toward the distal end of catheter 12 where part of it is received by the optical fibers 20 which define fiber-optic bundle 18. Preferably, a conventional wide angle objective lens system 54 is disposed at the distal end of the bundle 18 to permit wide angle viewing. The light thus received is transmitted through fibers 20 to the proximal end of bundle 18 and then to suitable observing means which may comprise, for example, a camera 6, ocular 8 or any other means for either viewing or recording the image conveyed from the distal end of the catheter. As presently preferred and shown, both camera 6 and ocular 8 are included in the preferred system 10. During insertion, the visibility is sufficient to monitor the position of the distal end of catheter 12 through the ocular 8.

When the distal end of the catheter 12 has reached the location at which exploration is desired, shown by way of example in FIG. 4 as the left atrium 58, the tubing 30 is then moved from the retracted position to an extended position in which the terminus of the head 36 protrudes at a distance of approximately 2 cm. beyond the distal end of the sheath 22. Movement of the tubing may be accomplished by a variety of means 61. For example, the proximal end of the tubing 30 may be secured to a suitable worm-gear arrangement (not shown) which may be operated by a calibrated knob 60.

It will be appreciated that during conventional cardiovascular endoscopy, the ability of the viewer to examine the cardiovascular system for constrictions, blockages, etc. has been impaired by the opaque medium, namely, blood, through which light from the source 65 must be transmitted and reflected to permit viewing. Because of such impaired viewing, the usefulness and reliability of prior art cardiovascular endoscopes has been greatly reduced. According to the present invention, however, a suitable physiologically innocuous clear solution, which may comprise, for example, a nine-tenths of one percent (0.9%) NaCl solution in distilled water, is injected through the tubing 30 by a conventional injection apparatus 3 where it is dispersed into the bloodstream through the apertures 40 in head 36. Because head 36 may be moved to an extended position, the clear solution may be dispersed in front of the distal end of the sheath 22. By suitably synchronizing the solution injections to coincide with pulsations of blood out from the heart 48 through aorta 46, the solution will be carried back toward the distal end of sheath 22 whereby the blood medium through which light from source 65 is normally transmitted and reflected will be momentarily replaced by the clear saline solution, thus permitting greatly improved viewing of the vessels and organs within the cardiovascular system.

In FIG. 1, injection apparatus 3 is in communication with the proximal end of the tubing 30. Pulse injection of the saline solution into the tubing 30 by injector 3 is controlled by a trigger pulse supplied by the EKG unit 4. EKG unit 4 is conventional, and may include, for example, a scope 17 for permitting visual display of the patient's EKG. Typically, the trigger pulse from the EKG will comprise the R portion of the QRS wave which may be detected, for example, by a conventional level detector. This trigger pulse is then delayed approximately 0.05 seconds by a conventional delay unit 5 before being transmitted to the injector 3. This delay is preferable since it permits injection of the saline solution into the blood stream when the flow rate of blood out from the heart 48 is at its maximum. Thus, injection of the saline solution into the bloodstream at this point insures that the solution will be carried rapidly back toward the distal end of the sheath 22 before the solution becomes dispersed thereby permitting viewing through a clear pocket of solution as the solution displaces the blood in front of the lens array 54. Typically, pressures in the aorta reach about 120 mm./hg. after the R-wave which means that injection pressures must exceed this pressure level. Injection pressures will preferably be about 300 mm./hg.

Medical equipment well known in the art is available to accomplish solution injection at a fixed point in the cardiac cycle. Thus, injector 3, EKG unit 4 and delay unit 5, which have been illustrated diagrammatically as separate components for purposes of illustration, may be replaced by V. H. Angiomat .model 3000 which includes a scope for displaying the patient's EKG, an injector head, and an adjustable delay for operating the injector at a fixed point during the cardiac cycle. The exact point in the cardiac cycle at which injection occurs is easily determined since the 3000-23 provides a marker, which appears as a negative spike in the cardiac trace upon each activation of injector head 3. Such equipment is designed to provide automatic control in which case injection occurs continuously at a fixed point in the cardiac cycle, or manual control, typically comprised of a push button or foot pedal, which permits manual triggering of the injection apparatus. Preferably, the operation of camera 6 will be synchronized with injection apparatus 3 by a conventional linear synchronization unit 7 such that images conveyed through the fiber-optic bundle 18 will be photographed only during periods of optimum viewing, i.e., as the saline solution is carried past the distal end of sheath 22.

Referring now to FIG. 5, visibility through ocular 8 is plotted as a function of time. Point A in FIG. 5 shows that the visibility is maximized just after injection of the saline solution into the bloodstream. Just before and just after injection, points B and C respectively, visibility is greatly reduced. Thus, FIG. 5 qualitatively illustrates the improved visibility which may be attained by employing the fiber-optic endoscopic catheter 12 of the present invention.

Skilled art workers will immediately recognize that each injection of solution into the bloodstream will tend to impart a jerking motion to the distal end of the catheter 12. Since the head 36 is extended during solution injection, such motion could cause the terminus 38 of head 36 to contact the endocardium with potentially damaging effect. To solve this problem, the distal portion of catheter 12 is preferably made more flexible than the remainder of the catheter. By way of example, the distal portion may be 12 cm. long. In addition, catheter 12 is preferably provided with two pairs of conventional angulation cords 72, 74 which extend between the distal and proximal ends of the catheter. Thus, once the catheter 12 has reached its desired location and the head 36 has been moved to the extended position, equal tensile forces may be applied to cord pairs 72, 74 at their proximal ends whereby the portion 70 may be secured in place during the injection procedure. Portion 70 is preferably made more flexible than the remainder of catheter 12 so that the distal end of the catheter will bend easily as it winds its way through the blood vessels and into the heart.

Referring now to FIGS. 6 and 7, a modified head 36' is shown. Head 36' is quite similar to head 36 illustrated in FIGS. 1 through 4, excepting that apertures 40' are located on the lateral sides of the head 36' instead of at the terminus thereof. This embodiment is useful when viewing locations disposed laterally of the catheter 12 since the particular arrangement of the apertures 40' shown in FIG. 6 insures that the saline solution will be dispersed radially outward from the head 36'. Thus, as the solution is carried back towards catheter 12, the solution will displace the blood in the region laterally spaced from the distal end of the sheath 22. Clearly, other arrangements of the apertures about head 36 to accommodate viewing other particular regions of the cardiovascular system are also possible.

It will be appreciated that numerous changes and modifications in the construction of system 10 and catheter 12 may be made without departing from the spirit and scope of this invention. For example, while lumen 24 has been shown and described as being centrally located within catheter 12, lumen 24 may be disposed at other locations, such as, for example, to one side of the center of the catheter. Moreover, while two afferent fiber-optic bundles 14 are shown and preferred in order to prevent head 36, when in the extended position, from blocking the radiation of light throughout the entire viewing region, a catheter constructed with one afferent fiber-optic bundle or more than two such bundles may also be employed. Similarly, more than one efferent fiber-optic bundle 18 may also be used. Moreover, while the particular arrangement of angulation cord pairs 72, 74 is preferred, skilled art workers will immediately recognize that other arrangements are also possible.

It is also possible to completely eliminate the head 36 and inject the solution into the cardiovascular system directly through the distal end of the tubing 30. Further, if desired, the distal end of the tubing 30 could be closed in which case the distal portion of the tubular member may be apertured which apertures would serve the same purpose as the apertures 40 in FIGS. 2 and 3.

Also, while the preferred system includes EKG unit 4, delay unit 5, camera 6 and linear synchronization unit 7, all or some of these components may be eliminated in which case system 10 would still have the capacity to perform its intended function. Of course, inasmuch as a visual record of the image conveyed to the ocular is desirable, a camera will normally be included. The camera, however, may be operated in ways other than those described above. For example, the shutter of the camera may be left open and the light source strobed at appropriate intervals. Strobing could be synchronized, for example, with fluid injections or, in the event injection is continuous, with a suitably selected point during the patient's heartbeat cycle. Preferably, manual control of the camera will be provided in order that pictures may be taken as and when desired by the operator of system 10.

Further, while the preferred system 10 has been described in conjunction with intracardiac endoscopy, it will be appreciated that the system 10 permits viewing at other locations. For example, through the cardiovascular system in FIG. 6, catheter 12 is being used to observe the operation of a valve 80 disposed in blood vessel 82. As shown, sheath 22 has been inserted into the blood vessel 82 until the distal face of the sheath is in confronting relation with valve 80. Head 36' is then moved into the extended position as is more fully described above until it protrudes through the valve. Because solution injection is synchronized with the R-wave portion of the EKG, the solution is carried along with the blood as the valve 80 opens to permit passage of blood therethrough thus insuring that the injected solution passes in front of lens array 54 during operation of valve 80.

Since these and other changes and modifications are within the scope of the present invention, the above description should be construed as illustrative and not in a limiting sense.

What is claimed is:

1. In an improved fiber-optic catheter for use in cardiovascular endoscopy of the type including a flexible sheath having a distal end and a proximal end, at least one afferent fiber-optic bundle disposed in said sheath for transmitting light from the proximal end of said catheter to the distal end thereof, and at least one efferent fiber-optic bundle disposed in said sheath for returning light from said distal end to said proximal end, the improvement comprising:

said catheter sheath having a longitudinally extending lumen therein and a rounded distal end face;

a tubular member having a distal portion, said distal portion having at least one aperture therein, said tubular member being mounted in said lumen for longitudinal sliding movement between a retracted position in which at least a major portion of said distal portion is received within said lumen and a position in which the free end of the distal portion of said tubular member is extended axially outward from the distal end face of said sheath, the free end of said distal portion being rounded, said rounded sheath end face and said rounded distal portion free end being shaped such that when said tubular member is in said retracted position said sheath and said distal portion free end define a uniformly curved surface; and means for restricting the proximal axial movement of said tubular member to said retracted position.

2. A fiber-optic catheter according to claim 1, wherein said lumen is centrally located within said sheath.

3. A fiber-optic catheter according to claim 2, including at least two afferent fiber-optic bundles, one of said afferent fiber-optic bundles being disposed on one side of said lumen, the other of said afferent fiber-optic bundles being disposed on the other side of said lumen.

4. A fiber-optic catheter according to claim 1, wherein the distal portion of said tubular member is removably secured to the remainder of said tubular member.

5. A fiber-optic catheter according to claim 1, wherein said at least one aperture is in the free end of said tubular member distal portion.

6. A fiber-optic catheter according to claim 5, wherein said at least one aperture is located in the side wall of said tubular member distal portion.

7. A fiber-optic catheter according to claim 1, further comprising means controllable from the proximal end of catheter for securing the distal portion of said sheath in a fixed position.

8. A fiber-optic catheter according to claim 7, wherein said securing means comprises a plurality of angulation cords disposed within said sheath and extending from the distal end of said sheath to the proximal end thereof.

9. A fiber-optic catheter according to claim 1, further comprising means for moving said tubular member between said retracted and extended positions.

10. A fiber-optic catheter according to claim 1, wherein said restricting means comprises:

said sheath having a radially extending shoulder in the interior wall thereof for defining a widened lumen portion at the distal end of said sheath; and said tubular member having a corresponding widened portion which seats on said shoulder when said tubular member is in said retracted position.

11. A fiber-optic catheter according to claim 10, wherein said widened portion is said distal portion.

12. A fiber-optic catheter system suitable for cardiovascular endoscopy comprising:

a flexible catheter having a proximal end and a distal end, said catheter including an annular sheath defining a lumen; at least one afferent fiber-optic bundle disposed in said sheath for transmitting light from the proximal end of said catheter to the distal end thereof; at least one efferent fiber-optic bundle disposed in said sheath for returning light from said catheter distal end to said catheter proximal end; a tubular member including a distal portion having at least one aperture therein, said tubular member being mounted in said lumen for longitudinal sliding movement between a retracted position in which at least a majority of said distal portion is received within said lumen and a position in which the free end of the distal portion of said tubular member is extended axially outward from the distal end face of said sheath;

a light source disposed at the proximal end of said afferent bundle;

means for injecting clear fluid into said tubular member for ejection through said at least one aperture when said tubular member is in said extended position;

means for generating a signal indicative of the fluid pressure in the cardiovascular system; and means responsive to the signal from said signal generating means for activating said injection means at a predetermined level of said signal.

13. A fiber-optic catheter system according to claim 12 and further comprising means for activating said fluid injection means at a fixed point during the cardiac cycle.

14. A fiber-optic catheter system according to claim 12 and further comprising an ocular disposed at the proximal end of said efferent fiber-optic bundle for viewing the image returned therethrough.

15. A fiber-optic catheter system according to claim 12 and further comprising means disposed at the proximal end of said efferent fiber-optic bundle for recording the image returned therethrough.

16. A fiber-optic catheter system according to claim 15 wherein said recording means is a camera.

17. A fiber-optic catheter system according to claim 12 and further comprising means disposed at the proximal end of said efferent fiber-optic bundle and synchronized with said fluid injection means for recording the image returned through said efferent fiber-optic bundle as said fluid injections pass by the distal end face of said sheath.

18. A fiber-optic catheter system according to claim 12, wherein said fluid injection means includes means for delaying injection of said fluid for a predetermined interval after said fluid injection means is activated.

19. A method of in situ visual examination of the cardiovascular system which comprises:

providing a catheter having a proximal end and a distal end, said catheter including an annular sheath defining a lumen; at least one afferent fiber-optic bundle disposed in said sheath for transmitting light from the proximal end of said catheter to the distal end thereof; at least one efferent fiber-optic bundle disposed in said sheath for returning light from said catheter distal end to said catheter proximal end; a tubular member including a distal portion having at least one aperture therein, said tubular member being mounted in said lumen for longitudinal sliding movement between a retracted position in which at least a majority of said distal portion is received within said lumen and a position in which the free end of the distal portion of said tubular member is extended axially outward from the distal end face of said sheath;

feeding said catheter into the cardiovascular system with said tubular member in said retracted position until the distal end of said catheter is in the vicinity of the portion of the cardiovascular system to be examined;

moving said tubular member to said extended position;

injecting a clear physiologically innocuous fluid into the cardiovascular system through said aperture in said tubular member whereby the blood flow in said vicinity carries said fluid in front of said efferent fiber-optic bundle to decrease the opacity of the fluid in said vicinity;

illuminating the portion of the cardiovascular system to be examined by illuminating the proximal end of said afferent fiber-optic bundle; and observing the image returned to the proximal end of said efferent fiber-optic bundle when said fluid is in front of the distal end thereof.

20. The method of claim 19 and further comprising the step of injecting said fluid into the cardiovascular system at a predetermined point during the cardiac cycle.

21. The method of claim 19 wherein the observing step is performed by visual observation of said image.

22. The method of claim 19 wherein the observing step is performed photographically.

* * * * *